(12) United States Patent
Spiekerkoetter et al.

(10) Patent No.: US 9,474,745 B2
(45) Date of Patent: Oct. 25, 2016

(54) USE OF FK506 FOR THE TREATMENT OF PULMONARY ARTERIAL HYPERTENSION

(75) Inventors: Edda Spiekerkoetter, Stanford, CA (US); Marlene Rabinovitch, Stanford, CA (US); Philip A. Beachy, Stanford, CA (US); David Solow-Cordero, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 243 days.

(21) Appl. No.: 14/113,375

(22) PCT Filed: Apr. 30, 2012

(86) PCT No.: PCT/US2012/035793
§ 371 (c)(1),
(2), (4) Date: Jan. 13, 2014

(87) PCT Pub. No.: WO2012/151153
PCT Pub. Date: Nov. 8, 2012

(65) Prior Publication Data
US 2014/0135358 A1   May 15, 2014

Related U.S. Application Data

(60) Provisional application No. 61/481,317, filed on May 2, 2011.

(51) Int. Cl.
*A61K 31/436* (2006.01)
(52) U.S. Cl.
CPC ................... *A61K 31/436* (2013.01)
(58) Field of Classification Search
None
See application file for complete search history.

(56) References Cited

U.S. PATENT DOCUMENTS

| 6,489,335 B2 | 12/2002 | Peyman |
| 2005/0119330 A1 | 6/2005 | Kao |
| 2007/0265294 A1 | 11/2007 | Kleinman |

FOREIGN PATENT DOCUMENTS

WO  2010031968  3/2010

OTHER PUBLICATIONS

Machado et al., Journal of the American College of Cardiology, 2009, vol. 54 (1), Supplement S, pp. S32-S42.*
Marlene Rabinovitch: "Pathobiology of Pulmonary Hypertension", Annual Review of Pathology: Mechanisms of Disease, pp. 369-399, vol. 2, No. 1, Feb. 1, 2007.
V. Albinana et al: "Immunosuppressor FK506 Increases Endoglin and Activin Receptor-ike Kinase 1 Expression and Modulates Transforming Growth Factor-1 Signaling in Endothelial Cells", Molecular Pharmacology, vol. 79, No. 5, pp. 833-843, Feb. 10, 2011.
Fujiwara. "Implications of Mutations of Activin Receptor-like Kinase 1 Gene (ALK1) in addition to Bone Morphogenetic Protein Receptor II Gene (BMPR2) in Children with Pulmonary Arterial Hypertension" Circ J (Jan. 2008), 72:127-133.
Yanik et al. "Tacrolimus (FK506) and methotrexate as prophylaxis for acute graftversus-host disease in pediatric allogeneic stem cell transplantation" Bone Marrow Transplantation (Jul. 2000), 26:161-167.
Hanaoka, et al., "Effect of Tacrolimus on Endotoxin-Induced Lung Injury in Sheep", Respir. Physiol. Neurobiol., Mar. 2002, vol. 130, No. 1, pp. 89-97.

* cited by examiner

*Primary Examiner* — James D Anderson
*Assistant Examiner* — Gregg Polansky
(74) *Attorney, Agent, or Firm* — Heslin, Rothenberg, Farley & Mesiti, PC

(57) ABSTRACT

A method of reducing pulmonary arterial hypertension in a mammal that employs FK506 is provided. In certain embodiments, the method comprises administering FK506 to a mammal having pulmonary arterial hypertension associated with defective MBPR2 signaling at a dosage sufficient to reduce blood pressure in the pulmonary artery of the mammal.

8 Claims, No Drawings

USE OF FK506 FOR THE TREATMENT OF PULMONARY ARTERIAL HYPERTENSION

GOVERNMENT RIGHTS

This invention was made with Government support under contracts HL089989, HL107450, TR000093, and RR025742 awarded by the Nation Institutes of Health. The Government has certain rights in the invention.

BACKGROUND

Pulmonary artererial hypertension is abnormally high blood pressure in the arteries of the lungs. Because symptoms may develop very gradually, patients may delay seeing a physician for years. Common symptoms are shortness of breath, fatigue, non-productive cough, angina pectoris, fainting or syncope, peripheral edema (swelling around the ankles and feet), and rarely hemoptysis (coughing up blood).

SUMMARY

A method of reducing pulmonary arterial hypertension in a mammal that employs FK506 is provided. In certain embodiments, the method comprises administering FK506 to a mammal having pulmonary arterial hypertension associated with defective BMPR2 signaling at a dosage sufficient to reduce blood pressure in the pulmonary artery of the mammal. In some cases, the mammal is a mouse, rat or a human. In particular cases, the mammal has hereditary pulmonary arterial hypertension caused by, for example, a mutation in BMPR2, ALK1 or endoglin. In particular cases the FK506 may be administered at a dose that provides an FK506 serum concentration of 0.05 to 1 ng/ml, e.g. 0.1-0.2 ng/ml.

DETAILED DESCRIPTION OF EXEMPLARY EMBODIMENTS

The method described herein is for treating pulmonary arterial hypertension in patients that have defect in BMPR2 (bone morphogenetic protein receptor 2) signaling. Pulmonary arterial hypertension (PAH) is a progressive lung disorder which, untreated, often leads to death on average within a few years after being diagnosed. An increasing constriction of the pulmonary circulation leads to increased stress on the right heart, which can develop into right heart failure. By definition, the mean pulmonary arterial pressure (mPAP) in a case of chronic pulmonary hypertension is >25 mmHg at rest or >30 mmHg during exertion, where the normal values are <20 mmHg. The pathophysiology of pulmonary arterial hypertension is characterized by vasoconstriction and remodeling of the pulmonary vessels. In chronic PAH there is neomuscularization of initially unmuscularized pulmonary vessels, and the vascular muscles of the already muscularized vessels increase in circumference. This increasing obliteration of the pulmonary circulation results in progressive stress on the right heart, which leads to a reduced output from the right heart and eventually ends in right heart failure (Humbert et al., J. Am. Coll. Cardiol. 2004, 43, 13S-24S).

Defects in BMPR2 signaling may, for example, be caused by a mutation in BMPR2 (see accession no. 600799 in NCBI's OMIM database), a mutation in ALK1 (the activin A receptor; see accession no. 601284 in NCBI's OMIM database) or a mutation in endoglin (see accession no. 131195 in NCBI's OMIM database). A defect in BMPR2 signaling can be detected, for example, by measuring the expression of Id1 (inhibitor of differentiation 1) mRNA or protein, which is a well-known downstream read-out for BMPR2 signaling. Decreased BMPR2 signaling decreases the amount of Id1 in pulmonary artery smooth muscle cells. In particular cases, the pulmonary arterial hypertension may be hereditary pulmonary arterial hypertension. In particular embodiments, a subject may be pre-screened to identify whether they have a mutation that effects BMPR2 signaling, or they may be assayed to determine if they have abnormal expression of Id1.

FK-506 (also known Tacrolimus or Fujimycin) is an immunosuppressive drug that is mainly used after allogeneic organ transplant to reduce the activity of the patient's immune system and so lower the risk of organ rejection. It is also used for the treatment of severe atopic dermatitis (eczema), severe refractory uveitis after bone marrow transplants, and the skin condition vitiligo. FK-506 is a 23-membered macrolide lactone discovered in 1984.

In T-cells, activation of the T-cell receptor normally increases intracellular calcium, which acts via calmodulin to activate calcineurin. Calcineurin then dephosphorylates the transcription factor NF-AT (nuclear factor of activated T-cells), which moves to the nucleus of the T-cell and increases the activity of genes coding for IL-2 and related cytokines. FK-506 prevents the dephosphorylation of NF-AT. Specifically, FK-506 reduces peptidyl-prolyl isomerase activity by binding to the immunophilin FKBP12 (FK506 binding protein) creating a new complex. This FKBP12-FK506 complex interacts with and inhibits calcineurin thus inhibiting both T-lymphocyte signal transduction and IL-2 transcription. In some embodiments, the FK506 is administered at a dose and regimen that provides an FK506 serum concentration that is much lower than the FK506 serum concentration commonly used in immunosuppressive applications (which is typically 5-15 ng/ml). For example, in certain embodiments of the instant method, the FK506 is administered at a dose and regimen that provides an FK506 serum concentration of as 0.05 ng/ml to 1 ng/ml, e.g., 0.1 ng/ml to 0.5 ng/ml, 0.15 ng/ml to 0.3 ng/ml or e.g. 0.1-0.2 ng/ml. In part because FK-506 is metabolized by the cytochrome P450 system, the exact dosing may vary between patients. The FK506 may be administered once a day or more, e.g., twice per day. In immunosuppressive applications, FK506 is normally given twice daily with the goal to reach FK-506 serum levels of 5-15 ng/ml. The treatment is started at 0.5 mg twice daily and then up-titrated according to the measured FK506 serum level. In some cases a dosing of 0.075 mg/kg/day is recommended to reach a serum levels of 5-10 ng/ml. In some embodiments of the instant method, the goal is to reach a serum level of about 0.2 ng/ml, which is about 1/20 of the immunosuppressive serum level. In this case, an initial dose of 0.001 mg/kg day to 0.01 mg/kg day (e.g., 0.002 mg kg/day to 0.05 mg/kg/day may be sufficient, and the does can be up-titrated according to the measured FK506 serum level. The subject may be any mammal, e.g., a human, rat, or mouse, for example. In particular cases, the FK506 may reach a serum concentration as low as 0.1-0.2 ng/ml (e.g., 0.10 to 0.12, 0.12 to 0.14, 0.14 to 0.16, 0.16 to 0.18 or 0.18 to 0.20, however serum a concentration in the range of 0.2 to 2 ng/ml, e.g., 0.2, 0.5, 1 and 2 ng/ml may be acceptable. In particular cases, the FK506 may reach a serum concentration of <1.0, 1.5-2.5, or 3-5 ng/ml.

The FK506 may be administered alone or in combination with other active compounds that treat or prevent PAH. The other active compound may be administered at a different time or at the same time as the FK506 and in certain embodiments the FK506 and the other active compound may be present in the same formulation, or as separate formulations in the same kit. Exemplary other active compounds that treat PAH include, e.g., prostacyclin analogues, endothelin receptor antagonists, phosphodiesterase-5 inhibitors, high-dose calcium channel blockers, anticoagulants, diuretics or antiproliferative agents. In particular cases, the other active compound may be, for example, Isordil (isosorbide dinitrate), Revatio (sildenafil), Tracleer (bosentan), Letairis (ambrisentan), Flolan (epoprostenol), Adcirca (tadalafil), Remodulin (treprostinil) Ventavis (iloprost), Tyvaso (treprostinil), Dilatrate-SR (isosorbide dinitrate), Isordil Titradose (isosorbide dinitrate), IsoDitrate (isosorbide dinitrate) or Isochron (isosorbide dinitrate).

Administration of FK506 to a subject may decrease pulmonary arterial pressure by about at least 1 mm Hg, e.g., at least 2 mm Hg, at least 3 mm Hg, at least 4 mm Hg, at least 5 mm Hg or at least 10 mm Hg or more, thereby returning the pulmonary arterial pressure to a level that may be considered normal for the subject.

In general terms, the FK506 may be administered to the subject in the instant method in a similar way to how FK506 is administered in immunosuppressive applications. For example, the FK506 may be present in a pharmaceutically acceptable excipient, and it may be administered intravenously. Alternatively, it may be administered orally.

Because the FK506 is being administered at a lower dose, its usual side effects may be decreased. Typical side effects include infection, cardiac damage, hypertension, blurred vision, liver and kidney problems (tacrolimus nephrotoxicity), hyperkalemia, hypomagnesemia, hyperglycemia, diabetes mellitus, itching, lung damage (sirolimus also causes lung damage), and various neuropsychiatric problems such as loss of appetite, insomnia, Posterior reversible encephalopathy syndrome, confusion, weakness, depression, cramps, neuropathy, seizures, tremors, and catatonia.

Pharmaceutical Compositions

A pharmaceutical composition comprising a subject compound may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A subject compound may be administered to the host using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations for pharmaceutical compositions are well known in the art. For example, Remington's Pharmaceutical Sciences, by E. W. Martin, Mack Publishing Co., Easton, Pa., 19th Edition, 1995, describes exemplary formulations (and components thereof) suitable for pharmaceutical delivery of disclosed compounds. Pharmaceutical compositions comprising at least one of the subject compounds can be formulated for use in human or veterinary medicine. Particular formulations of a disclosed pharmaceutical composition may depend, for example, on the mode of administration and/or on the location of the infection to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the affliction being treated can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in Remington's Pharmaceutical Sciences, 17th Edition, Mack Publishing Company, Easton, Pa., 1985. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are solidified at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules).

Methods of preparing such dosage forms are known, or will be apparent, to those skilled in the art.

Certain embodiments of the pharmaceutical compositions comprising a subject compound may be formulated in unit dosage form suitable for individual administration of precise dosages. The amount of active ingredient administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

Methods of Administration

The route of administration may be selected according to a variety of factors including, but not necessarily limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a subject compound will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated.

Therapeutically effective doses (or growth inhibitory amounts) of a subject compound or pharmaceutical composition can be determined by one of skill in the art, with a goal of achieving local (e.g., tissue) concentrations that are at least as high as the IC50 of an applicable compound disclosed herein.

The specific dose level and frequency of dosage for any particular subject may be varied and will depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

In order to further illustrate the present invention, the following specific examples are given with the understanding that they are being offered to illustrate the present invention and should not be construed in any way as limiting its scope.

Example I

Mouse Study

Background

A loss of function mutation in bone morphogenetic protein (BMP) receptor II (BMPRII) is present in >80% of familial and ~20% of sporadic idiopathic (I) PAH (Machado et al. Hum Mutat 2006, 27:121-32). Even patients with IPAH without a BMPRII mutation or with other causes of PAH have reduced expression of BMPRII, reinforcing the importance of BMPRII signaling in the pathogenesis of PAH (Humbert M et al. Eur Respir J 2002, 20:518-23). Furthermore BMPR2 receptor gene therapy attenuates experimental hypoxic pulmonary hypertension in rats (Reynolds et al. Am J Physiol Lung Cell Mol Physiol 2007). Therefore increasing BMPRII signaling in patients with pulmonary arterial hypertension might prevent or reverse disease.

Methods

3600 FDA approved drugs and bioactive compounds were screened for their ability to activate BMP signaling, using a C2C12 mouse myoblast cell line stably transfected with a reporter plasmid expressing a BMP response element (BRE) from the Id1 promoter fused to the luciferase-gene (BRE-luc). Whether the best qHTS-BMPRII activator can induce Smad phosphorylation (phospho), Id1 expression and promote PAEC survival and tube formation was determined using BMP4 as a positive control. Whether the qHTS-BMPRII-activator would prevent PAH in mice with a conditional deletion in BMPRII in ECs (BMPRII-SCL-Cre-ERT) that develop exaggerated PAH after 3 weeks of hypoxia (10% $O_2$) was determined. In order to assess whether the BMPRII activator could also reverse PAH, we used 2 models of severe experimental PH in rats: 1. Monocrotaline induced pulmonary hypertension with development of severe medial hypertrophy of the pulmonary arteries 3 weeks after injection. 2. SUGEN (VEGF-Receptor blocker) and 3-week chronic hypoxia induced pulmonary hypertension with development of neointima formation in pulmonary arteries 8 weeks after initiation of the stimulus. Both groups were treated with FK-506 for 3 weeks via sc osmotic pump (0.05 mg/kg/d) after PAH and remodeling of the pulmonary arteries was established. The serum level of FK-506 in mice and rats was aimed to be 0.2 ng/ml.

Results

FK-506, an agent that can induce BMPRIA phosphorylation, was the main activator of Id1 expression. FK-506, at a dose of 15 ng/ml, the therapeutic serum level used to induce immunosuppression, and at a much lower dose of 0.2 ng/ml increased Id1 protein expression 1 h following stimulation, in a manner comparable to BMP4 (10 ng/ml) (n=3, p<0.06). This was preceded by phospho-Smad 1/5/8 at 15 min, similar to BMP4 (n=3, p<0.001). FK-506 induced p-Smad 1/5/8 and Id1 expression in PAECs harvested from six different IPAH patients at the time of transplant, including 3/6 patients that did not respond to BMP4. Both BMP4 and FK-506 improved survival of PAECs (n=5, p<0.001) and induced tube formation in an angiogenesis assay (n=3, p<0.01). A 3-week preventive treatment with FK-506 (0.05 mg/kg/d) (serum levels 0.2 ng/ml) in mice with a conditional deletion in BMPRII in ECs exposed to 3 weeks of hypoxia prevented the development of PAH and right ventricular hypertrophy (RVH); RV systolic pressure: 32±0.9 vs 21±2.3 mmHg, p<0.001; RVH: 36.2±2.5 vs 26.9±4.5, p<0.01, both n=5. To test whether FK-506 could also reverse PAH, we induced PAH in rats with monocrotaline (60 mg once s.c) and began treatment with FK-506 3 weeks after injection, a time when PAH was established (RVSP 50.8±2.7 mmHg, n=7). The survival after a 3-week treatment with FK-506 did not differ in the FK-506 (57%) compared to the vehicle group (66%), yet of those that that survived the PAH was significantly reduced after treatment with FK-506 compared to vehicle treated animals (RVSP 39.5±4.7 vs 68.6±4.2 mmHg, n=14).

It was determined that the combined stimulus of SUGEN (20 mg/kg s.c) and 3-weeks of chronic hypoxia induced PAH in rats when rats were returned to RA and left for another 5 weeks (RVSP 55.1±10.7 vs control 25.1±0.5 mmHg, RVH 0.24±0.005 vs 0.44±0.07, n=4, p<0.05) but that a 3-week sc treatment of FK-506 at the time of established PAH could prevent progression and induce regression of PAH in FK-506 treated vs vehicle treated animals (RVSP 66.5±4.1 mmHg vs 39.5±0.6 mmHg, RVH 0.49±0.07 vs 0.34±0.02, n=4, p<0.05). Neointima formation in small pulmonary arteries (alveolar wall and alveolar duct vessels) per total vessel number decreased from 61.2±6.1% to 16.2±5.8% (n=4, p<0.01). At the low dose of FK-506 of 0.2 ng/ml no effect on total or differential WBC count was observed, nor was an immunosuppressive effect of decreased nuclear NFATc2 measured.

Conclusion

FK-506 (Tacrolimus) was identified in a quantitative high throughput screen (qHTS) of FDA approved drugs and bioactive compounds as a drug that activates BMPRII signaling, restores normal function of pulmonary artery endothelial cells (PAECs), prevents and reverses experimental PAH in mice and rats.

Example 2

Clinical Study

Patients are invited to participate in this study because they have pulmonary hypertension (PH) and are currently treated with one or multiple drugs for PH such as PDE-5 inhibitors (sildenafil, tadalafil), prostacyclins (Flolan, Remodulin, Iloprost) and/or the endothelin antagonist Ambrisentan. While all these drugs are effective as vasodilators, new medications are sought that could reverse the pathological remodeling of the pulmonary arteries. Whether subjects have a familial form of pulmonary hypertension or not, it is known that a certain pathway (BMPR2) is impaired in PH. Studies have shown that the immunosuppressive drug FK-506 (Tacrolimus) activates the BMPR2 pathway and prevents and reverses pulmonary hypertension in experimental pulmonary hypertension.

This study is open to male or female subjects, 18-70 years of age, with PH. If a patient agrees to participate in this study, the patient will be one of 40 subjects participating in the study.

If a patient agrees to participate and the patent qualifies, the patient will be allocated to the study drug through a process called randomization. Randomization means that the study drug that the patient will receive is selected by chance (like the flip of a coin). The study drug options for this study are placebo, and 3 different doses of FK-506 (blood level <1.0, 1.5-2.5, and 3-5 ng/ml; as a reference: the immunosuppressive dose is 5-15 ng/ml). The study drug will be added to the patient's baseline PH therapy. The randomization for this study is 1:3 which means patients have a chance of 75% of receiving treatment with FK-506.

The purpose of this study is to confirm that adding FK-506 to a PH treatment at a dose below the normal dose that is used for immunosuppression is safe and whether it will improve pulmonary hypertension. Heart function will be assessed by echo, 6-min walk and the biomarker NT-proBNP.

Study Medication

FK-506 (Tacrolimus) is an FDA approved immunosuppressive drug used in organ transplantation as well as in autoimmune diseases. As the metabolism of FK-506 differs in patients quite widely, therapy is directed by measuring drug levels in whole blood. The blood will be drawn shipped to a testing lab to measure FK-506 levels. The goal immunosuppressive doses are 5-15 ng/ml. In this study we aim for much lower doses (see above). Patients will receive the study drug for the duration of study. The drug will be delivered in a prepared bottle, which allows monitoring of drug intake. This device is called a Medication Event Monitoring System (MEMS) and for it to monitor drug intake properly. Patients should always take out one tablet at a time from the bottle.

Participation in the study lasts for approximately 16 weeks. During this time, patients will be required to visit the clinic approximately 4-5 times.

Study Procedures

If a patient agrees to take part in this study, they will first sign this consent form. After the patients have signed, dated and received a copy of this consent form, they will have the study screening visit to ensure the patient is eligible to take part in this study. Previous test results (echocardiogram, physical examination, pulmonary function tests, Right Heart Catheterization (RHC) may also be used to determine patient eligibility.

What is claimed is:

1. A method of reducing pulmonary arterial hypertension in a mammal, comprising: administering FK506 to a mammal having pulmonary arterial hypertension associated with defective BMPR2 signaling, wherein said FK506 is administered at a dosage that results in a blood concentration of FK506 between 0.1 ng/mL and 5 ng/mL.

2. The method of claim 1, wherein said mammal is human.

3. The method of claim 1, wherein said mammal has reduced expression of BMPR2, ALK1 or endoglin.

4. The method of claim 1, wherein said mammal has hereditary pulmonary arterial hypertension caused by a mutation in BMPR2.

5. The method of claim 1, wherein said mammal has hereditary pulmonary arterial hypertension caused by a mutation in ALK1.

6. The method of claim 1, wherein said mammal has hereditary pulmonary arterial hypertension caused by a mutation in endoglin.

7. The method of claim 1, wherein said dosage provides an FK506 blood concentration of 0.1-0.2 ng/ml.

8. The method of claim 1, wherein said administering is oral or inhalation.

* * * * *